US010827930B2

(12) United States Patent
Kakileti et al.

(10) Patent No.: US 10,827,930 B2
(45) Date of Patent: Nov. 10, 2020

(54) PRIVACY BOOTH FOR BREAST CANCER SCREENING

(71) Applicant: Niramai Health Analytix Pvt Ltd, Bangalore (IN)

(72) Inventors: Siva Teja Kakileti, Andhra Pradesh (IN); Geetha Manjunath, Bangalore (IN); Krithika Venkataramani, Bangalore (IN)

(73) Assignee: NIRAMAI HEALTH ANALYTIX PVT LTD, Bangalore (IN)

( * ) Notice: Subject to any disclaimer, the term of this patent is extended or adjusted under 35 U.S.C. 154(b) by 1236 days.

(21) Appl. No.: 15/055,011

(22) Filed: Feb. 26, 2016

(65) Prior Publication Data
US 2017/0245762 A1 Aug. 31, 2017

(51) Int. Cl.
*A61B 5/00* (2006.01)
*B25J 9/00* (2006.01)
*B25J 19/02* (2006.01)
*B25J 13/06* (2006.01)
*A61B 90/50* (2016.01)
*A61B 34/30* (2016.01)
*A61B 5/01* (2006.01)

(52) U.S. Cl.
CPC .......... *A61B 5/0046* (2013.01); *A61B 5/0075* (2013.01); *A61B 5/0091* (2013.01); *A61B 5/015* (2013.01); *A61B 34/30* (2016.02); *A61B 90/50* (2016.02); *B25J 9/0084* (2013.01); *B25J 13/065* (2013.01); *B25J 19/023* (2013.01); *A61B 5/0013* (2013.01); *A61B 5/7405* (2013.01); *A61B 5/7475* (2013.01); *A61B 2562/0204* (2013.01)

(58) Field of Classification Search
CPC ............ A61B 2562/0204; A61B 34/30; A61B 5/0013; A61B 5/0046; A61B 5/0075; A61B 5/0091; A61B 5/015; A61B 5/7405; A61B 5/7475; A61B 90/50; B25J 13/065; B25J 19/023; B25J 9/0084
See application file for complete search history.

(56) References Cited

U.S. PATENT DOCUMENTS

| 5,999,843 | A | * | 12/1999 | Anbar | ..................... | A61B 5/015 600/474 |
| 2004/0011284 | A1 | * | 1/2004 | Schucker | ............... | B25J 19/023 118/688 |
| 2010/0123078 | A1 | * | 5/2010 | Guinta | ................... | A61B 5/015 250/334 |

(Continued)

Primary Examiner — Amelie R Davis

(57) ABSTRACT

What is disclosed is an apparatus for enabling privacy for patients undergoing breast cancer screening in a non-clinical setting. One embodiment of the present apparatus comprises an enclosure in which a person can remove one or more garments to expose their breasts to a thermal camera for breast cancer screening. The enclosure is such that at least the breast area of that person is shielded from view by third parties. The apparatus also comprises a thermal camera for capturing thermal images of the exposed breast area. The thermal camera is connected to a robotic arm that changes the camera angle relative to real-world coordinates so that thermal images can be taken of the breast area from any angle between a frontal view and a left/right lateral view. A processor which executes a software interface tool for semi-automated or automated breast cancer screening based on the thermal images of the breast.

17 Claims, 8 Drawing Sheets

(56) References Cited

U.S. PATENT DOCUMENTS

| | | | | |
|---|---|---|---|---|
| 2010/0312136 | A1* | 12/2010 | Cozzie | A61B 5/015 600/549 |
| 2013/0010081 | A1* | 1/2013 | Tenney | A61B 34/30 348/47 |
| 2013/0173287 | A1* | 7/2013 | Cashman | E04H 3/08 705/2 |
| 2015/0051461 | A1* | 2/2015 | Dalal | A61B 5/02427 600/323 |
| 2015/0200996 | A1* | 7/2015 | Ziarati | H04L 67/02 709/201 |
| 2015/0293596 | A1* | 10/2015 | Krausen | B25J 13/02 606/130 |

* cited by examiner

PRIVACY BOOTH FOR BREAST CANCER SCREENING

TECHNICAL FIELD

The present invention is directed to an apparatus for enabling privacy for a person (man or woman) undergoing breast cancer screening in a non-clinical setting.

BACKGROUND

More than 25 percent of cancer deaths among women is caused by breast cancer. Research shows that early detection can increase a patient's chances for survival. Current screening devices consist of either a simple thermal camera or a device that includes thermal cameras and coolers to cool the breast region before screening. Thermography based breast cancer screening is gaining popularity as it can be more convenient and as accurate as traditional mammographic techniques. It is non-contact and painless, and can screen tumors without side effects. It should be appreciated that the equipment used for this screening requires the female to undress to waist in front of a technician so that radiometric images of the breast can be taken. The lack of privacy can be a primary reason why many women preferring not to undergo breast cancer screening. This has the adverse affect of limiting the uptake of women undergoing such screening, and further hampering the ability to screen for early stage cancers. With the advent of mass screenings arising in remote areas of developing countries like India where screening can take place in a van or a bus, devices that provide privacy to women in this regard are increasingly desirable.

Accordingly, what is needed in this art is an apparatus for enabling privacy for a person undergoing breast cancer screening in a non-clinical setting.

BRIEF SUMMARY

What is disclosed is an apparatus for enabling privacy for enabling privacy for a person (man or woman) undergoing breast cancer screening in a non-clinical setting. One embodiment of the present apparatus comprises an enclosure which enables a person to be able to remove garments to expose a breast area for breast cancer screening while being shielded from view by third parties. The apparatus comprises a thermal camera for capturing thermal images of the exposed breast area. The thermal camera is connected to a robotic arm that changes the camera angle ($\varphi$, $\theta$, $\omega$) relative to a set of real-world reference coordinates so that thermal images can be captured of the breast area from any angle between a frontal view and a left/right side view. The apparatus further comprises a processor which executes machine readable program instructions for implementing a software interface tool for semi-automated or automated breast cancer screening based on an analysis of the thermal images of the patient's breast. Features and advantages of the above-described apparatus will become apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

Figure 1:
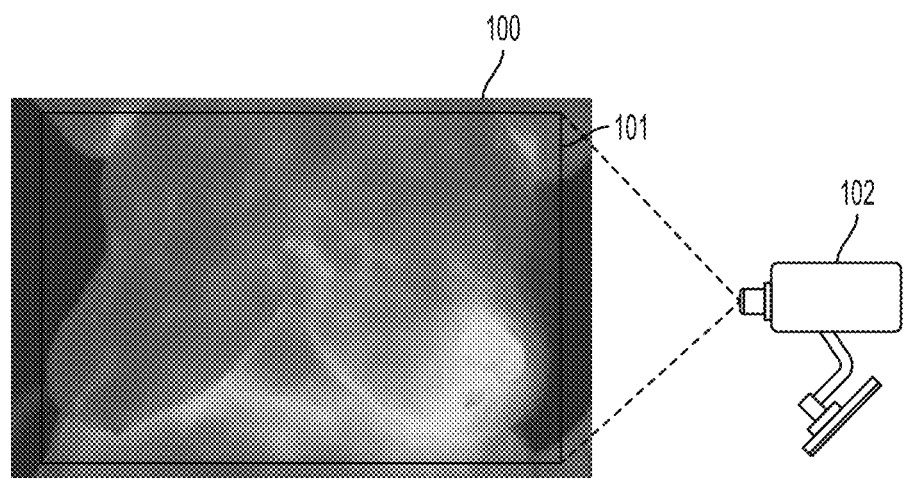
FIG. 1 shows an example thermal imaging of the exposed breast area of a woman undergoing breast cancer screening in accordance with the teachings hereof.

What is disclosed is a system and method is an apparatus for enabling privacy for a person undergoing breast cancer screening in a non-clinical setting.

A "patient" is a living being. The patient can be a man or a woman. As such, gender pronouns are not to be viewed as limiting the scope of the appended claims strictly to female patients. Moreover, although the term "person" or "patient" may be used interchangeably throughout this disclosure, it should be appreciated that the patient undergoing breast cancer screening in accordance with the teachings hereof may be something other than a human such as, for example, a primate. Therefore, the use of such terms is not to be viewed as limiting the scope of the appended claims to humans.

A "breast area" refers to tissue of the breast and may further include surrounding tissue as is deemed appropriate for breast cancer screening. Thermal images are capture of the breast area in various view angles.

A "thermal image" is an image which comprises a matrix of pixels each having an associated temperature value. Pixels in the thermal image with a higher temperature value are displayed in the thermal image with a first color and pixels with a lower temperature value are displayed in a second color. Pixels with temperature values between the lower and higher temperature values are displayed in gradations of color between the first and second colors. Thermal images are communicated to a workstation which runs a computer program for processing the thermal images using a software interface tool designed to perform semi-automated or fully-automated screening of thermal images for tumor detection or classification. Thermal images are captured or are otherwise acquired using a thermal camera.

A "thermal camera" refers to either a still camera or a video camera with a lens that focuses infrared energy from objects in a scene onto an array of specialized sensors which convert infrared energy into electrical signals on a per-pixel basis and outputs a thermal image comprising an array of pixels with color values corresponding to temperatures of the objects in the image across a desired thermal wavelength band. The thermal camera can be any of: a single-band infrared camera, a multi-band infrared camera in the thermal range, and a hyperspectral infrared camera in the thermal range. The resolution for a thermal camera is effectively the size of the pixel. Smaller pixels mean that more pixels will go into the thermal image giving the resulting image higher resolution and thus better spatial definition. Although thermal cameras offer a relatively large dynamic range of temperature settings, it is preferable that the camera's temperature range be relatively small, centered around the person's body surface temperature so that small temperature variations are amplified in terms of pixel color changes to provide a better measure of temperature variation. Thermal cameras are readily available in various streams of commerce. Use of the term "image" is intended to also mean "video". In one embodiment, the thermal camera is placed in wired or wireless communication with a workstation which enables manual or automatic control of various aspects of the thermal camera such as, for instance, adjusting a focus of the thermal camera lens, changing a resolution of the thermal camera, and changing a zoom level of the thermal camera, some or all of which may be integrated with a software interface tool for performing breast cancer screening based on the thermal images of the person's breast area.

Figure 2:
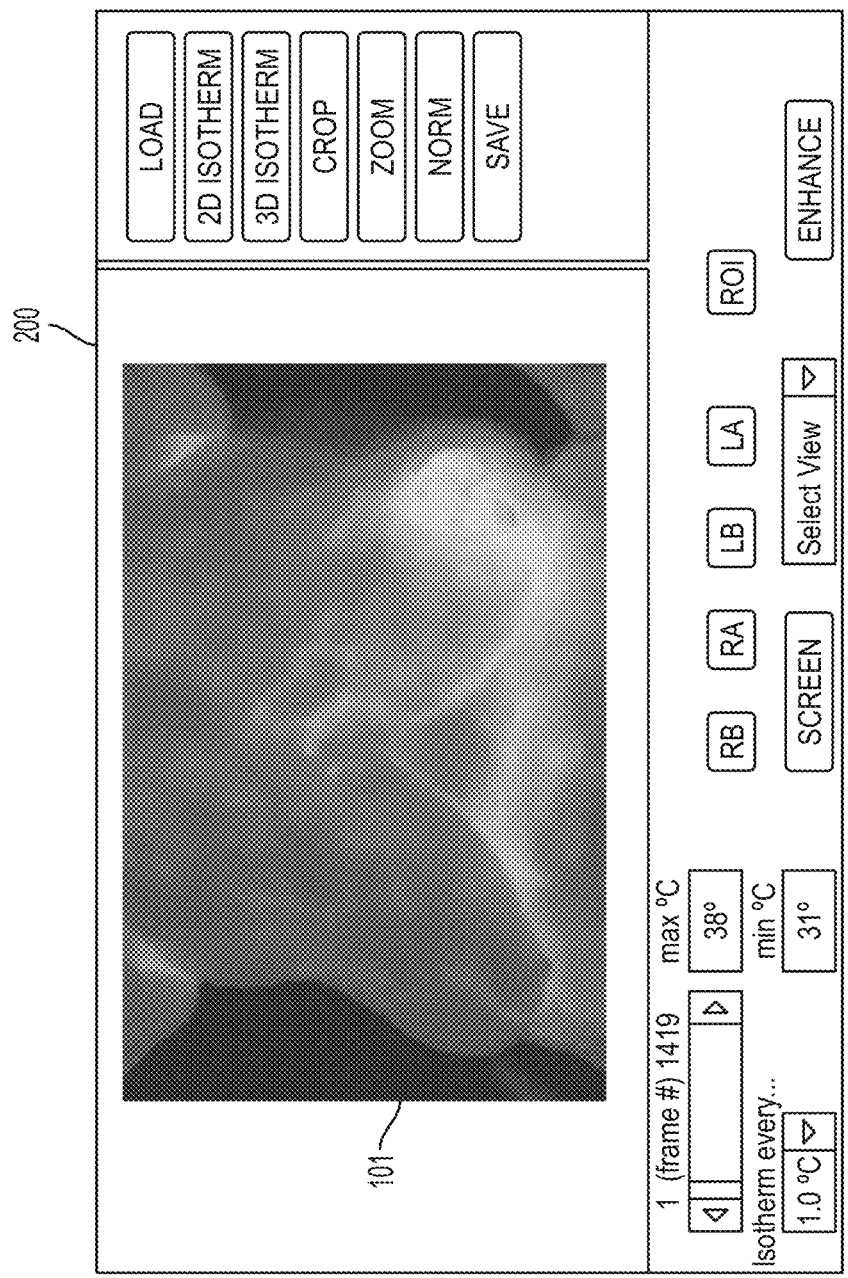
FIG. 2 shows one example embodiment of a software interface tool for performing breast cancer screening based on a thermal image of the patient's breast area of FIG. 1.

A "software interface tool" is a composite of functionality for tumor detection and/or tumor classification using a plurality of user-selectable objects displayed on a display device such as a touchscreen display. FIG. 2 shows one example menu screen of a software interface tool 200 for analyzing the thermal image 101. One embodiment of a software interface tool which implements a tumor detection method is disclosed in commonly owned and co-pending U.S. patent application Ser. No. 14/668,178, entitled: "Software Interface Tool For Breast Cancer Screening", by Krithika Venkataramani et al. Another embodiment of a software interface tool which implements a tumor classification method is disclosed in commonly owned and co-pending U.S. patent application Ser. No. 15/053,767, entitled: "Software Interface Tool For Breast Cancer Screening", by Gayatri Sivakumar et al. Various embodiments of the software interface tool perform manual, semi-automatic, and automatic selection of a block of pixels in the thermal image for screening based on differences in temperature values between a given block of pixels and temperature values of pixels in surrounding tissue. The present apparatus further comprises a robotic arm. The software interface tool may be configured to enable the manual or automatic selective manipulation of a robotic arm connected to the thermal camera.

Figure 3:
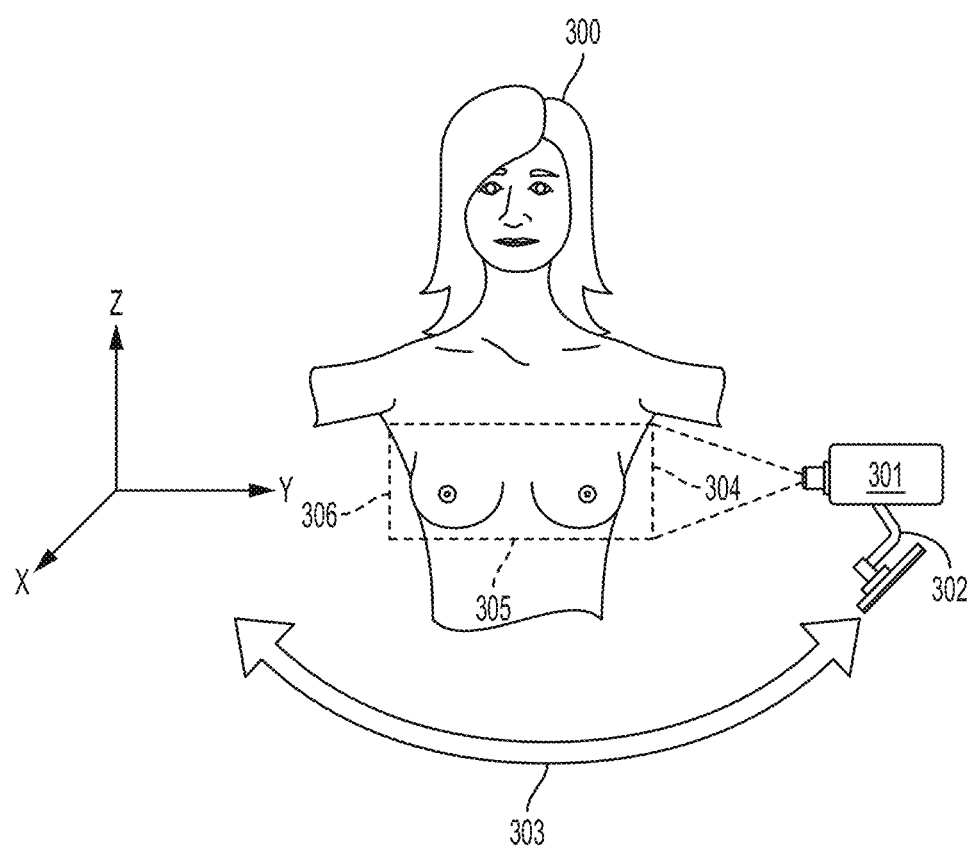
FIG. 3 shows an example female patient with a thermal camera mounted on a slideable and axially rotatable robotic arm for moving the camera along a semi-circular trajectory from side-to-side in the front of the patient.
Figure 4:
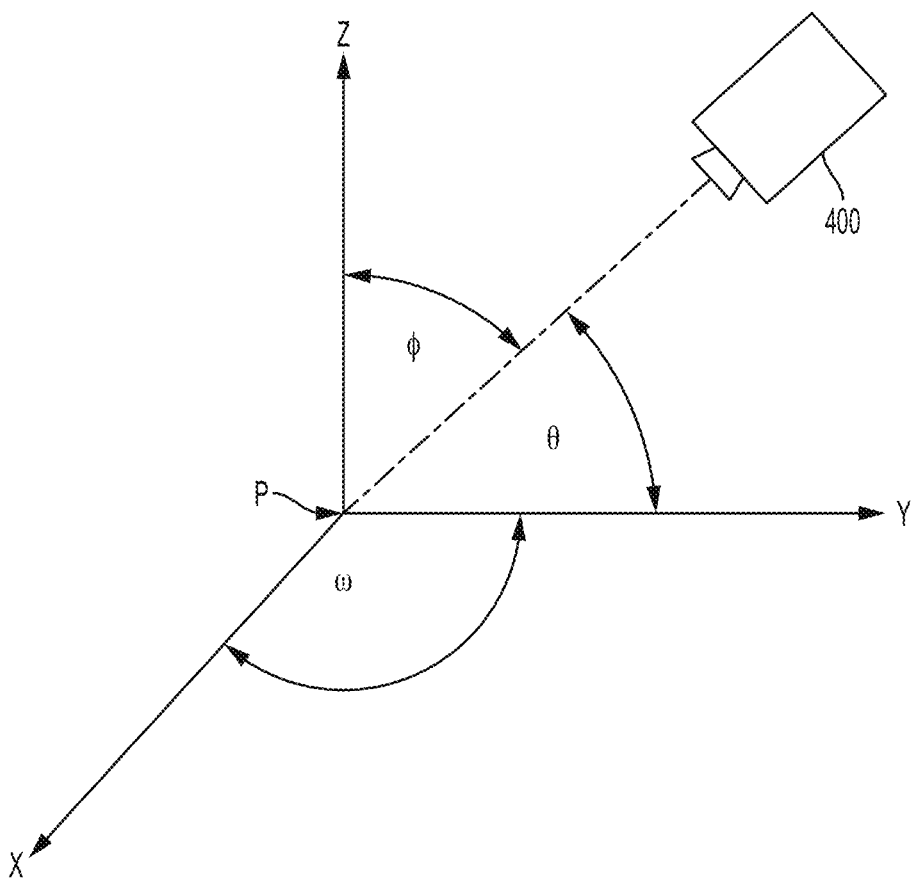
FIG. 4 shows the various camera angles that can be effectuated by the robotic arm of FIG. 3 relative to a set of real-world reference coordinates.

A "robotic arm" is functions to manipulate a movement of the thermal camera to enable the image acquisition of a desire view angle. Common view angles for image acquisition include a craniocaudal view, mediolateral view, mediolateral oblique view, and lateral view. FIG. 3 shows an example female patient 300 with a thermal camera 301 mounted on a slideable and axially rotatable robotic arm 302 capable of moving the camera along a semi-circular trajectory 303 from side-to-side in the front of the patient such that thermal images can be captured in a right-side view 304, a front view 305, and a left-side view 306, and any angles in between. As shown in FIG. 4, the robotic arm moves the camera 400 to angle ($\varphi$, $\theta$, $\omega$) relative to the X, Y and Z axis of real-world reference coordinates. The robotic arm effectuates a movement of the thermal camera 400 to effectuate a camera rotation reaching at least (90°, 90°, 0°), (90°, 0°, 90°), and (0°, 90°, 90°) in order to enable the acquisition of images from a top-side of the breast and an underside of the breast, and view angles therebetween. It should be appreciated that the images acquired are centered relative to a desired targeted area at point P. The robotic arm may be placed in wired or wireless communication with a joystick or game controller, for example, which enables a user to selectively manipulate a movement of the robotic arm, as desired. A workstation, in wired or wireless communication with the robotic arm, may be configured to execute machine readable program instructions which enable a user to manually or automatically selectively manipulate the robotic arm as desired. In accordance with the teachings hereof, an enclosure is utilized in conjunction with the thermal camera and robotic art.

Figure 5:
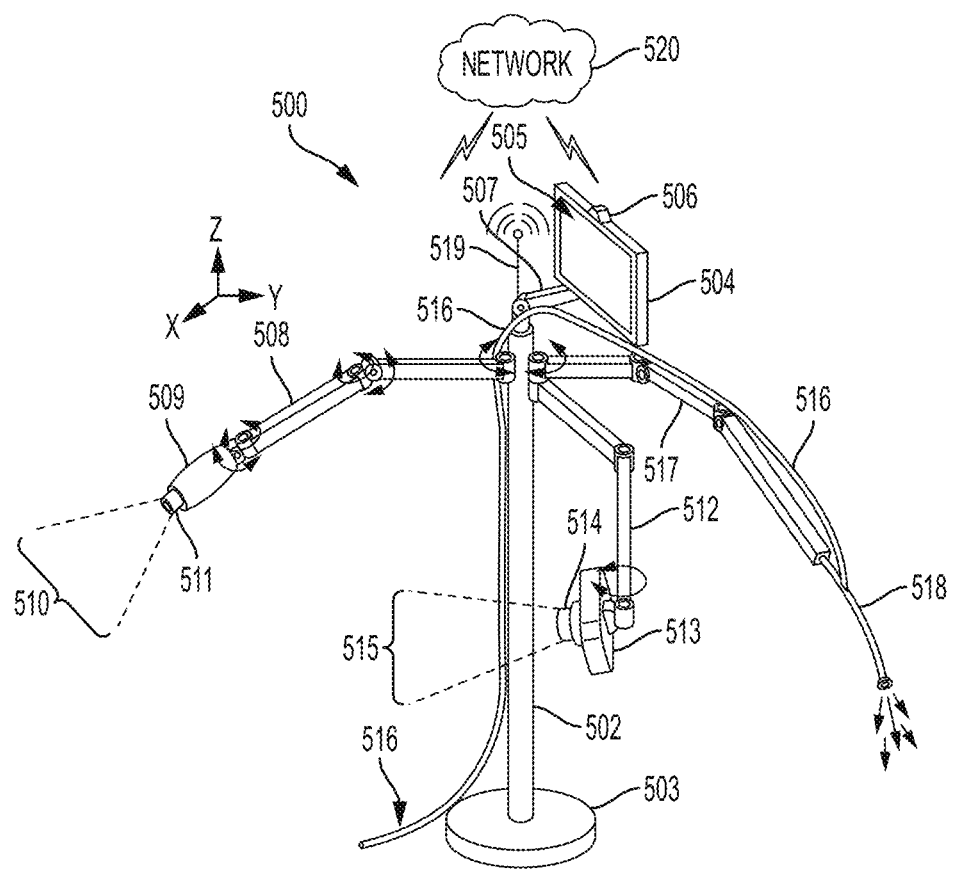
FIG. 5 shows one embodiment with a plurality of robotic arms mounted on a stationary support post fixed to a base which rests on a set of wheels so that the device can be physically moved.

Reference is now being made to FIG. 5 which shows one embodiment, generally at 500, with a plurality of robotic arms mounted on a stationary support post 502 fixed to a base 303 which rests on a set of wheels (not shown) or a track (not shown) so that the device can be physically or automatically moved or repositioned. In other embodiments, the support post is fixed to a floor, wall, or ceiling of the enclosure.

Fixed to a top portion of the support post is display 504 shown as a touchscreen device 505 whereon various messages, images, information, instructions, results, and the like, can be displayed. Display 504 further is configured with a speaker 506 which, in part, comprises a sound system for playing audio music, messages, instructions, and the like. Display 504 is rotatably mounted to robotic arm 507 so that the touchscreen 505 can be turned in any of a plurality of directions for optimum viewing and optimal use by a user thereof.

Support post 502 has another robotic arm 508 attached to a thermal video camera 509 with a telescopic lens 510. Robotic arm 508 is remotely controllable so that a position of the thermal video camera 509 affixed to an end thereof is selectively adjustable to move in any of a plurality of directions relative to the real-world reference coordinates (X, Y, Z). In such a manner, a position of the thermal video camera 509 can be adjusted so that thermal video can be obtained of the patient's breast area, as desired, which in the camera's field of view, at 510. Operation of the thermal video camera 509 and the telescopic lens 511 are also remotely controllable.

Support post 502 is further configured with another robotic arm 512 whereon a thermal camera 513 with a telescopic lens 214 is mounted. Robotic arm 512 is remotely controllable so that a position of the thermal camera 513 affixed to an end thereof is selectively adjustable to move in any of a plurality of directions relative to the real-world reference coordinates (X, Y, Z). In such a manner, a position of the thermal camera 512 can be adjusted so that thermal images can be obtained of the patient's breast area, as desired, which are in the camera's field of view, at 515. Operation of the thermal camera 512 and the telescopic lens 514 are also remotely controllable.

Support post 502 is further configured with a robotic arm 517 whereon a remotely controllable air nozzle 518 is affixed. Air nozzle 518 is connected to an air hose 516 which feeds cold compressed air from a compressor (not shown) into the air nozzle. In various embodiments hereof, the air nozzle is directed to move over a desire area and blast a jet of cold air (set at a predetermined temperature) onto a surface of an area of exposed skin tissue to lower the thermal signature thereof.

All of the devices and robotics arms are remotely controllable by a workstation or by the software interface tool executing machine readable program instructions which control one or more device controllers in a manner which is well understood in the software arts. Robotic arms which can rotate in any of a plurality of directions are readily available from different vendors in various streams of commerce. Many such robotic arms are remotely controllable via a wired or wireless communication protocol.

Transmitter 519, shown as an antenna, effectuates bi-directional communication with various remote devices over network 520. The transmitter 217 may utilize a wired connection consisting of cables and a hub placed in communication with one or more remote devices over network 520. Any of the devices of the diagnostic system of FIG. 2 may include various elements for communicating with remote devices over network 520. Techniques for placing devices in networked communication are well established. As such, a further discussion as to specific techniques for networking devices has been omitted.

Figure 6:
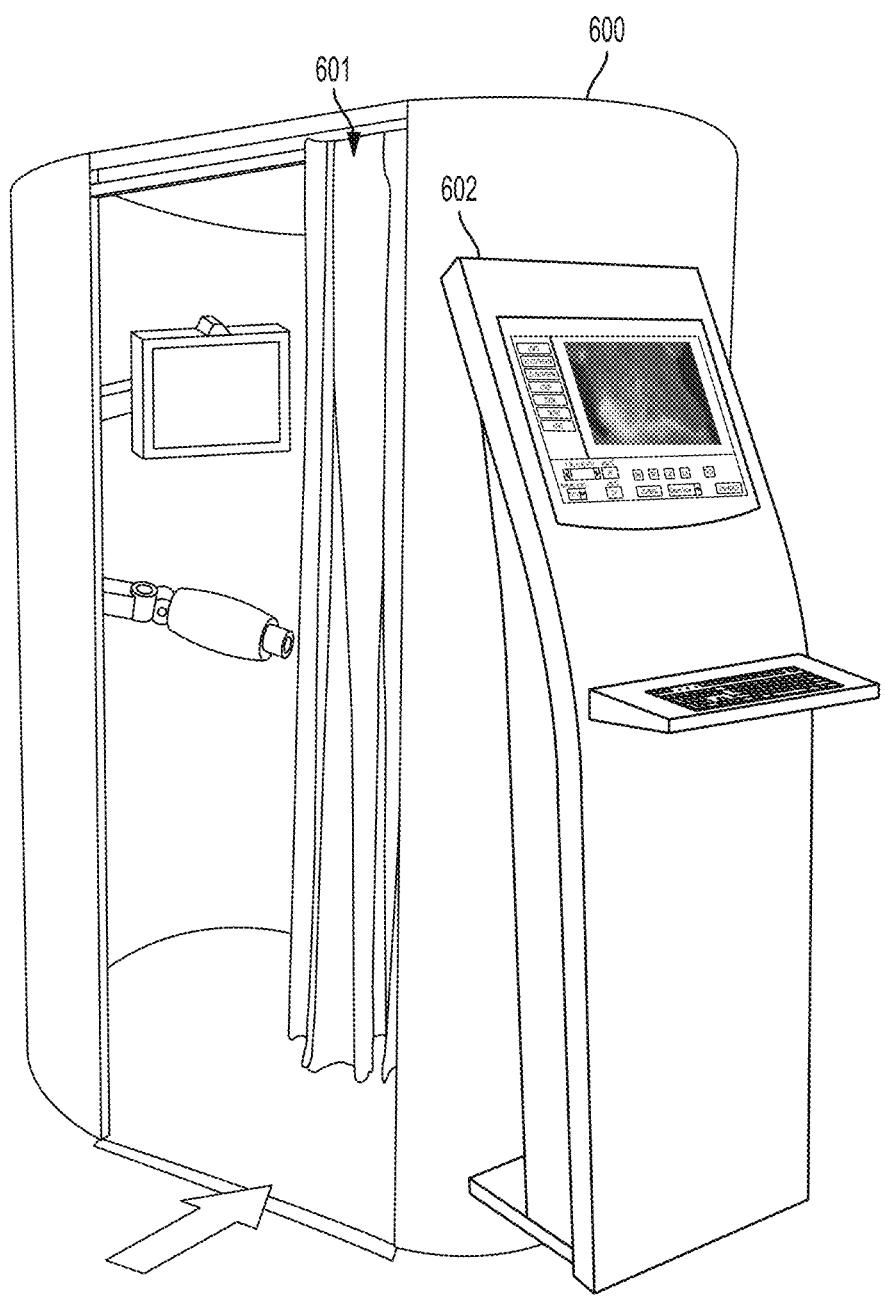
FIG. 6 shows a privacy booth with a retractable privacy curtain wherein various aspects of the embodiment of FIG. 5 are mounted.

An "enclosure" shields the patient's exposed breast area from view by third parties. The enclosure may take the form of a booth with retractable curtains where a patient physically enters and removes their garments to expose their breast to a thermal camera for breast cancer screening. The thermal camera(s) may be mounted on a wall, ceiling, or floor of the booth. FIG. 6 shows a privacy booth 600 with a retractable curtain 601 wherein various aspects of the embodiment of FIG. 5 are mounted. An operator thereof utilizes the kiosk-like workstation 602 to control the breast cancer screening process and perform various aspects of the embodiments hereof with the operator providing instructions, guidance and assistance to the patient inside the booth, as needed. The kiosk-like workstation 602 may be placed next to the privacy booth 600 or may be integral to an interior or an exterior wall of the privacy booth. The kiosk-like workstation may be remotely located with respect to a location of the privacy booth 600. Both the kiosk-like workstation and the privacy booth may be configured to be portable to they can be easily disassembled, transported to a remote location such as a remote village, and re-assembled for patient breast cancer screening.

Figure 7:
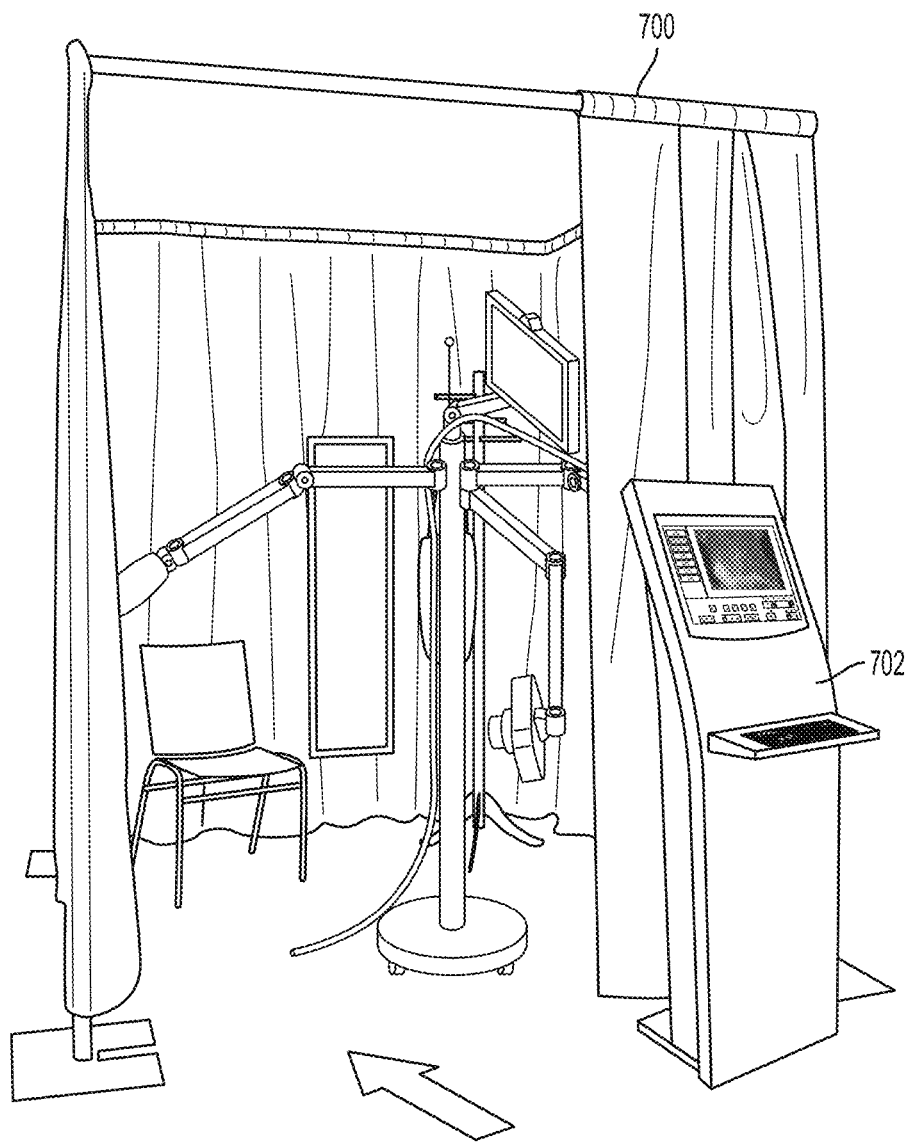
FIG. 7 shows another embodiment of a privacy booth with a retractable privacy curtain wherein the embodiment of FIG. 5 can be positioned as desired.

FIG. 7 shows another embodiment of a privacy booth 700 with a retractable privacy curtain wherein the embodiment of FIG. 5 can be maneuvered and positioned as desired. The kiosk-like workstation 702 can be positioned inside or outside the privacy booth of FIG. 7 or placed adjacent thereto. The kiosk-like workstation may be remotely located with respect to a location of the privacy booth. Both the kiosk-like workstation and the privacy booths of FIGS. 6 and 7 may be disassembled, transported to a remote location, and re-assembled for patient screening. The enclosure of FIG. 7 is shown with a chair, mirror, and a clothes rack for patient convenience. The enclosures may contain a bed, recliner, stool, and the like which can be utilized by the patient during thermal image acquisition. The patient may stand, sit, recline or lay down depending on the patient's needs and the design of the enclosure.

The enclosure may further incorporate various aspects of a sound system for communicating with the patient or for playing background music. A microphone and a video screen may be utilized to visually and audibly enable communication to/from the patient. Such communication may take the form of pre-made video instructions indicating what the patient needs to be doing at any given point in time during the image acquisition process. A light or an alarm may be used to signal when the breast cancer screening has completed. A Braille interface and other features and functions to make the enclosure handicap friendly and handicap accessible can also be included. Because the amount of black-body radiation emitted by an object increases with the object's temperature, variations in temperatures of objects may be readily observable in a thermal image. Therefore, it should be appreciated that the enclosure is made of a suitable material that limits thermal interference. The enclosure may be further outfitted with a cooling apparatus for projecting chilled air, such as compressed air, onto the skin tissue of the breast area to lower the surface tissue's thermal signature.

In operation, a patient seeking breast cancer screening approaches or enters the booth. Medical information is obtained from the patient either by an operator or by the patient answering various questions using the touchscreen display. Instructions displayed on a display screen (or by other means such as, for instance, audio messages) which inform the patient where to stand, sit, lie down, or otherwise position themselves. Video images are then captured using the thermal camera at one or more views of the breast area, as shown and discussed with respect to FIG. 3 using various embodiments of, for example, FIG. 5. The thermal images are transmitted over network 520 to a workstation (such as the kiosk-like workstation of FIGS. 6 and 7) which may reside in a remote facility. A technician or medical practitioner views the transmitted images and communicates with the subject using one or both of the display screen 504 and the speaker 506. The medical practitioner can further instruct the patient to, for instance, stand still or extend their arms in a certain manner or position themselves in a manner as desired depending on the configuration of the privacy booth so that more or better thermal images can be acquired. The technician remotely controls the positioning and operation of the thermal camera. In another embodiment, the positioning and operation of the thermal camera are automatically controlled by an artificial intelligence program operating in conjunction, in whole or in part, with the software interface tool performing the breast cancer screening. Once adequate images in the desired view angles have been obtained from the patient, the patient thereafter be instructed via audio or visual messaging and/or by an alarm such as a bell or light, which provides an indication that the screening process has completed and they can leave the booth at their convenience. The thermal images are processed either semi-automatically or automatically by the software interface tool run by the kiosk-like workstation, depending on the implementation.

Image processing algorithms, which may include a face detection algorithms, pose detection algorithms, positions of body features, and the like may be used to guide the automatic adjustment of the relative position between any of the thermal cameras and the breast area undergoing examination. Upon identifying the breast area using such algorithms and methods, a position of the camera can be moved accordingly and thermal images or thermal videos acquired. Alternatively, the subject is instructed to move the breast to a particular position so that the thermal camera can obtain the desired images. In another embodiment, both a position of the subject and the thermal camera are adjusted accordingly so that the desired measurements can be obtained.

Once the software interface tool has completed tumor detection and/or tissue classification, the results thereof can be displayed on the display of the kiosk-like workstation or transmitted to a medical practitioner for review and to confirm diagnosis, if possible. The medical practitioner may directly communicate with the person in the booth to let them know that further testing is required, or that nothing unusual was detected during screening.

It should be appreciated that the nature and extent of the analysis performed using the thermal images of the breast area will necessarily depend on the medical issues presented by the patient. Therefore, a discussion with respect to a particular analysis has been omitted. It should also be appreciated that the configurations and components discussed herein may be supplemented with other devices used to acquire patient measurements such as, for example, sphygmomanometer to acquire blood pressure readings, a respirometer to determine respiration rate, and a thermometer to obtain a temperature measurement.

EXAMPLE WIRELESS NETWORKED SYSTEM

Figure 8:
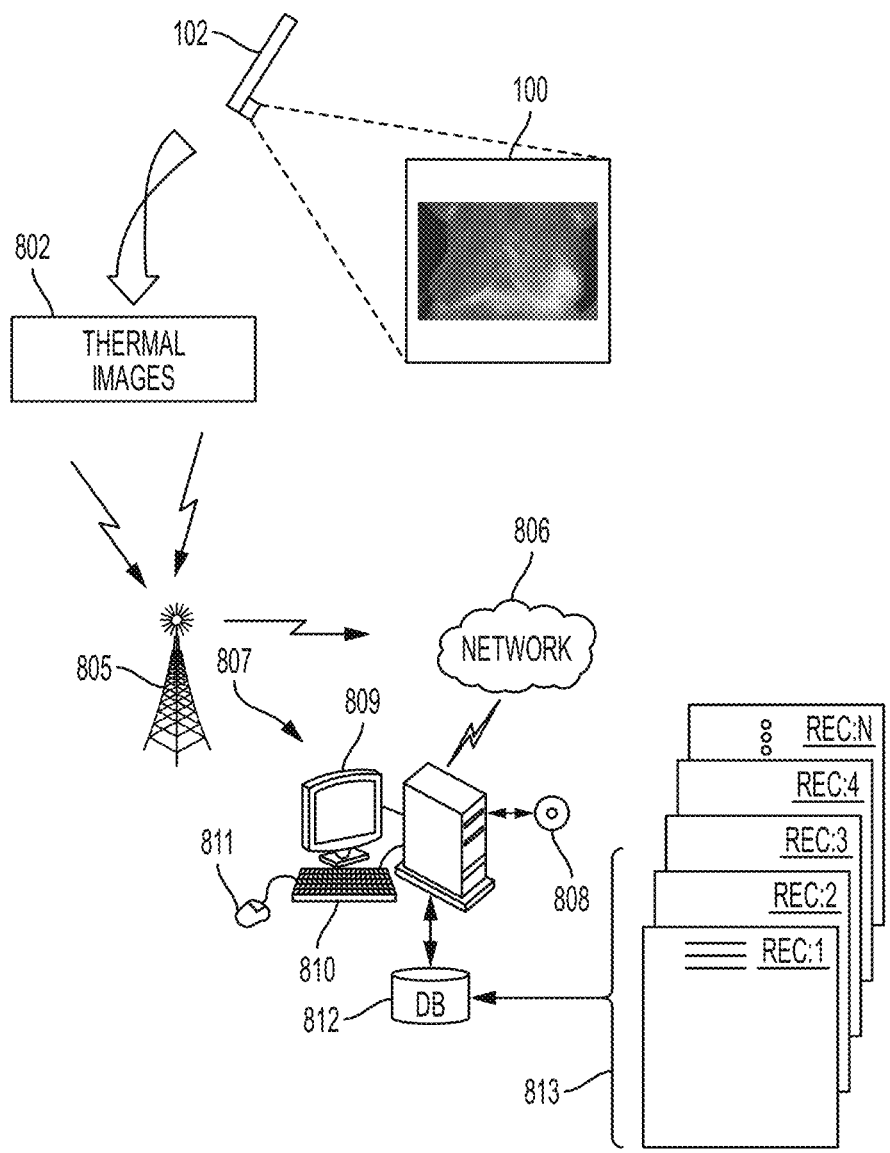
FIG. 8 is a block diagram of one example networked system for performing various aspects of the teachings disclosed herein.

Reference is now being made to FIG. 8 which shows a block diagram of one example networked system for performing various aspects of the teachings disclosed herein. The embodiment shown is illustrative and should not be viewed as limiting the scope of the appended claims strictly to this configuration.

In FIG. 8, thermal camera 102 is shown capturing a thermal image 101 of a patient's breast area. A plurality of thermal images (collectively at 802) are wirelessly communicated to a cellular communication tower 805 which transmits the thermal image frames to a server (not shown) on a network 806. A remote computing device, shown as a workstation 807, is communicatively coupled to the network via wired or wireless pathways. Such a workstation may be in a remote location some distance away from the location of the privacy booth wherein the thermal images were acquired.

The workstation has a computer case which houses various components such as a motherboard with a processor and memory, a network card, a video card, a hard drive capable of reading/writing to machine readable media 808 such as a floppy disk, optical disk, CD-ROM, DVD, magnetic tape, and the like, and other software and hardware needed to perform the functionality of a workstation, as is widely understood. A hard drive, internal to the computer case, stores mathematical formulae, functions, and the like, as need for performing region of interest identification, pixel isolation, temperature determination, temperature comparison, and the like. The workstation further includes a display screen 809, such as a CRT, LCD, or touchscreen device. Thermal images, temperature values, rates of change, threshold levels, including other patient vitals such as heart rate, respiration rate, blood pressure, to name a few, can be displayed on the display screen. A medical professional can use the display to monitor the patient during the screening process. Values, algorithms, variables, results of interim calculations, and the like, performed by the workstation can also be displayed. A user or technician can view any of the received information and make selections from displayed menu options. Keyboard 810 and mouse 811 effectuate a user input or selection.

Database 812 contains records (collectively at 813). Records stored in the database can be manipulated, updated, and retrieved in response to a query. Information stored on these records takes the form of patient medical histories associated with breast cancer and cancers in general, temperature values, thermal images, to name a few. Such records may also include information identifying patients, diagnoses, prognoses, and treatments. Although the database is shown as an external unit of hardware, the database may be internal to the workstation mounted, for example, on a hard disk housed in the computer case.

It should be appreciated that the workstation has an operating system and other specialized software configured to display alphanumeric values, menus, scroll bars, dials, slideable bars, pull-down options, selectable buttons, and the like, for entering, selecting, modifying, and accepting information needed for processing the thermal image frames in accordance with the methods disclosed herein for breast cancer screening. The user interface can be utilized to set parameters, select images or portions thereof for processing, identify one or more regions of interest, set threshold levels, adjust camera settings, etc. These selections, including the received video image frames and other signals, may be stored to storage devices 808 and 812. Default settings and initial values and other parameters can be retrieved from either the storage devices. A practitioner may further utilize the workstation to communicate instructions back to the user depending on the implementation, to instruct them, for instance to take steps, perform actions, or so that video can be acquired from a different perspective or to zoom-in on a particular region of the breast area.

Results may be communicated to other practitioners for their review and input over the wireless network 806 and/or the cell tower 805. The received images, diagnoses, results, and the like, can be communicated to other professionals, secondary or tertiary service providers and government agencies, depending on the implementation. Various aggregate summaries can be computed using patient data. These include, but are not limited to: longitudinal analyses involving statistics of patient cases; population-based studies of patients within one or more sub-populations; geography-based studies involving patients in specified geographical areas; and socio-economic and community-based studies involving patients in a specified social or economic community. By combining knowledge of genetics, more sophisticated modeling and analyses can also be performed to assess risk for breast cancer from a genetic standpoint.

It should be appreciated that some or all of the functionality performed by the workstation may be performed, in whole or in part, by a laptop or tablet-PC. Although shown as a workstation, it can be an ASIC, tablet, notebook, laptop, server, or mainframe. The embodiment of the workstation is illustrative and may include other functionality known in the arts. The teachings hereof can be implemented in hardware or software using any known or later developed systems, structures, devices, and/or software by those skilled in the applicable art without undue experimentation from the functional description provided herein with a general knowledge of the relevant arts.

One or more aspects of the methods described herein are intended to be incorporated in an article of manufacture. The article of manufacture may be shipped, sold, leased, or otherwise provided separately either alone or as part of a product suite or a service. The above-disclosed and other features and functions, or alternatives thereof, may be desirably combined into other different systems or applications. Presently unforeseen or unanticipated alternatives, modifications, variations, or improvements may become apparent and/or subsequently made by those skilled in this art which are also intended to be encompassed by the following claims. The teachings of any publications referenced herein are hereby incorporated by reference in their entirety.

What is claimed is:

1. An apparatus for enabling privacy for a patient for automated breast cancer screening in a non-clinical setting, the apparatus comprising:

an enclosure which shields an exposed breast area of the patient for the automated breast cancer screening from view by third parties;

a thermal camera for capturing a thermal image of the exposed breast area;

a first robotic arm for changing an angle of the thermal camera relative to an axis of a set of real-world reference coordinates;

an air nozzle that is attached to a second robotic arm, wherein the air nozzle is connected to an air hose which feeds cold air from a compressor into the air nozzle, wherein the air nozzle blows a jet of cold air onto a surface of the exposed breast area to improve a thermal signature thereof; and a processor that is configured to
  (i) automatically adjust a focus of the thermal camera, (ii) automatically change a zoom level of the thermal camera and (iii) automatically manipulate the first robotic arm connected to the thermal camera to position the thermal camera, for capturing the thermal image of the exposed breast area; and
  execute a computer program which implements a software interface tool, wherein the software interface tool implements a tumor detection method for performing breast cancer screening based on the captured thermal image of the exposed breast area.

2. The apparatus of claim 1, further comprising any of: a sound system, a microphone, and an alarm for signaling when the screening has completed.

3. The apparatus of claim 1, further comprising a joystick for enabling a user to selectively manipulate the first robotic arm.

4. The apparatus of claim 1, wherein the enclosure is such that a patient can physically enter the enclosure and remove garments of the patient to expose their breasts for breast cancer screening while the breasts remain shielded from view by persons outside the enclosure.

5. The apparatus of claim 1, wherein the processor is configured to execute machine readable program instructions for signaling that screening for breast cancer has completed.

6. The apparatus of claim 1, wherein the processor is integral to the thermal camera.

7. The apparatus of claim 1, wherein the first robotic arm enables thermal images to be taken of the exposed breast area in any view angle from a frontal view to a side view.

8. The apparatus of claim 1, wherein the processor is in communication with the thermal camera via a wireless connection.

9. The apparatus of claim 1, wherein the software interface tool enables the automatic selection of a block of pixels in the thermal image for screening, manipulates a robotic arm controller to move the thermal camera and adjusts the thermal camera zoom or focus so that a region of interest in a desired view angle is at least semi-automatically zoomed into.

10. The apparatus of claim 1, further comprising a video monitor that is configured to display instructions for the patient.

11. The apparatus of claim 1, further comprising at least one of: a rotatable chair in which the person can sit, and a rotatable disc on which the person can stand.

12. The apparatus of claim 1, wherein the enclosure comprises a material which does not interfere with the acquisition of thermal images.

13. The apparatus of claim 1, wherein the enclosure is portable.

14. The apparatus of claim 1, wherein the processor is in a workstation.

15. The apparatus of claim 14, wherein the workstation is a kiosk workstation.

16. The apparatus of claim 15, wherein the kiosk workstation is integral to the enclosure.

17. The apparatus of claim 1, wherein the processor is configured to execute machine readable program instructions for communicating with a medical professional located a distance from the enclosure.

* * * * *